United States Patent [19]
Jörnéus

[11] Patent Number: 5,145,371
[45] Date of Patent: Sep. 8, 1992

[54] DISTANCE MEMBER

[75] Inventor: Lars Jörnéus, Göteborg, Sweden

[73] Assignee: Nobelpharma AB, Goteborg, Sweden

[21] Appl. No.: 581,711

[22] Filed: Sep. 14, 1990

[30] Foreign Application Priority Data

Sep. 15, 1989 [SE] Sweden ............................... 8903038

[51] Int. Cl.$^5$ ................................................. A61C 8/00
[52] U.S. Cl. .................................... 433/173; 433/174
[58] Field of Search ............... 433/173, 174, 175, 220, 433/221

[56] References Cited

U.S. PATENT DOCUMENTS

| | | | |
|---|---|---|---|
| 4,850,870 | 7/1989 | Lazzara .............................. | 433/173 |
| 4,850,873 | 7/1989 | Lazzara et al. ..................... | 433/220 |
| 4,988,298 | 1/1991 | Lazzara et al. ..................... | 433/173 |
| 5,040,983 | 8/1991 | Binon ................................. | 433/174 |

FOREIGN PATENT DOCUMENTS 8905498 7/1989 Fed. Rep. of Germany .
1281470 10/1972 United Kingdom .

*Primary Examiner*—Gene Mancene
*Assistant Examiner*—Nicholas D. Lucchesi
*Attorney, Agent, or Firm*—Pollock, Vande Sande & Priddy

[57] ABSTRACT

The invention relates to a distance member (1) for a tooth implant anchored in the jaw, which distance member comprises, on the one hand, a sleeve-shaped element (5) which is designed to connect with the shoulder part of the securing element (fixture) (2) of the tooth implant and, on the other hand, a distance screw (7) provided with an externally threaded part (8) for engaging in a bore (9) in the upper part of the fixture for anchoring the sleeve-shaped distance element (5) on the fixture (2). The distance screw (7) is provided with an upper bore (25) for securing of a cap (4) embedded in the prosthesis construction. The upper part of the distance member is designed to be accommodated within a conical, upwardly narrowing delimiting surface defined by the said cap (4). The upper part (17) of the sleeve-shaped element has a conical peripheral surface (18) with an engagement part (14) designed to cooperate with a tubular counterstay (29) in a fitting tool, and the distance screw (7) also has a conical peripheral surface which forms an extensions of the conical upper part (17) of the sleeve-shaped element, and which has an external engagement part designed to cooperate with a second part, a tightener (27) in the fitting tool. The design of the distance member permits a low distance height and facilitates handling.

7 Claims, 3 Drawing Sheets

DISTANCE MEMBER

BACKGROUND OF THE INVENTION

The present invention relates to a distance member for a tooth implant anchored in the jaw, which distance member comprises, on the one hand, a sleeve-shaped element which is designed to connect with the shoulder part of the securing element (fixture) of the tooth implant and, on the other hand, a distance screw provided with an externally threaded part for engaging in a bore in the upper part of the securing element for anchoring the sleeve-shaped element on the securing element, and the distance screw being provided with an upper bore for securing of a prosthesis construction It is already known to permanently anchor dental bridges in the bone tissue of the jaw with the aid of screw-type securing elements, so-called fixtures, made of titanium The method which has been found to afford the greatest anchoring stability and which has been used clinically with good results for over 20 years is the so-called osseointegration method developed by Professor Per-Ingvar Brånemark and co-workers and described, for example, in Brånemark/Zarb/Albrektsson: "Tissue-Integrated Prostheses", Quintessence Book, 1985.

The method is based on a very exact and atraumatic technique for insertion of the fixtures in such a way that a direct contact, that is to say an exact fitting between the fixture and the bone tissue. Such a direct contact between the fixture and the bone tissue provides the best conditions for a truly permanent anchoring of, for example, a dental prosthesis.

The screw-type fixtures of pure titanium are introduced into the jaw in a first operation, which is followed by an unloaded healing phase of critical length, during which the fixture is covered by intact mucous membrane. During this healing phase the bone tissue grows onto and forms one unit with the implanted fixture. In a second operation the fixture is then exposed and an essentially cylindrical distance member is arranged on the fixture with the aid of a distance screw. The bridge construction itself is then anchored on the distance member with the aid of fixing screws which in turn are secured in the distance screws.

The tubular distance members which are used in connection with the anchoring of dental bridges are designed in various lengths. The Brånemark system marketed by Nobel-pharma AB. includes, as standard components, distance members having lengths from 3 mm and upwards.

There is a need to be able to introduce shorter distance members, that is to say distance members which are also less than 3 mm upon anchoring of dental bridges. A low distance height is in fact of great importance in obtaining aesthetically acceptable prosthetic constructions where the titanium surface of the implant cannot be seen above the gum of the patients. The term distance height here refers to the space between the connection surface of the distance member with the shoulder part of the fixture and the connection surface with the gold cylinder which is embedded in the bridge construction.

However, for technical reasons, it is not possible to retain current design and reduce the height of the distance members. The reason for this is that there must be room in the distance screw for an internal thread which is at least 2 mm long. The dental prosthesis is in fact screwed into position in this thread with the aid of gold screws.

Another reason why it is not possible to reduce the height of a distance member of the current design is that such a distance member would be very difficult to handle. The distance member would then only consist of a very short distance sleeve with a height of only about 1–2 mm.

Swedish Patent 8701949-3 already discloses a distance member which is used in connection with the anchoring of single-tooth prostheses, that is to say individual teeth. In this case also the distance member comprises a tubular distance element and a distance screw provided with an externally threaded part which engages in the bore of the securing element and in this way anchors the tubular distance element. The screw connection has a special design provide increased anchoring stability and withstand high torsional loads which can arise in single-tooth replacements.

The tubular distance member is elongate since its upper part is designed to form a frame for the single-tooth prosthesis. Such a distance member cannot be used together with a dental bridge of the type which comprises embedded conical gold cylinders. Nor is it possible to screw a gold cylinder firmly in the distance screw.

SUMMARY OF THE INVENTION

An important purpose of this invention is to provide a distance member with a low distance height, where the distance member is at the same time designed in such a way that its handling is facilitated.

A further aim of the invention is to provide a distance member which is adapted to be embedded conical gold cylinders present in the bridge construction.

The invention will be described in greater detail below with reference to the attached drawings which show one preferred embodiment of the present invention distance member.

DETAILED DESCRIPTION OF THE PREFERRED EMBODIMENT

Figure 1:
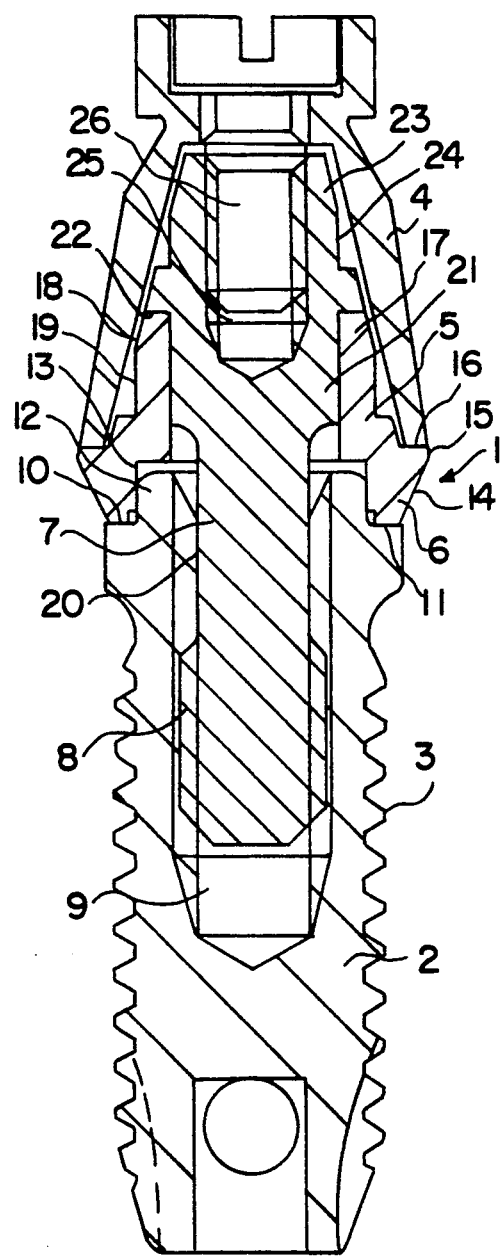
FIG. 1 shows a longitudinal section through a tooth implant in the form of a fixing screw (fixture), the distance member according to the invention and a gold cylinder.

FIG. 1 shows a distance member 1 according to the invention anchored on a securing element in the form of a cylindrical screw (fixture) 2 of titanium with an external thread 3 designed to be introduced into a previously drilled hole in the jaw for permanent anchoring of a dental bridge. The dental bridge is connected to the distance member via a gold cap 4 embedded in the dental bridge. Both the fixture 2 and the gold cap 4 consist of components which are already known and are therefore not described in great detail here.

The distance member 1 comprises, on the one hand, a substantially sleeve-shaped element 5 whose base part 6 connects with the shoulder part of the fixture and, on the other hand, a distance screw 7 for securing the sleeve-shaped element on the fixture To this end, the distance screw is provided with a threaded part 8 which engages in an internally threaded bore 9 in the upper part of the fixture.

The upper part of the fixture has in a known manner an annular collar 10 against which the base part of the sleeve-shaped element bears with a corresponding bearing surface 11 and a hexagonal engagement part 12 in order to permit engagement of an associated tool for threading the fixture down into the previously drilled hole in the jaw. The base part 6 of the distance sleeve is provided with a corresponding internal hexagonal recess 13 which cooperates with the engagement part 12 of the fixture The base part 6 of the sleeve-shaped element has an external, downwardly narrowing conical part 14, and a possibly cylindrical part 15 whose length can be varied. The lower conical and possibly cylindrical part bears against the gum and forms a biological seal against the latter.

The sleeve-shaped element moreover has an outer, annular collar 16 which forms the bearing surface against the conical gold cylinder 4 embedded in the dental bridge.

The upper part of the sleeve-shaped element is designed as a conical, tubular part 17 and is accommodated within the conical delimiting surface which is defined by the gold cylinder 4. The conical peripheral surface 18 has an external hexagonal recess 19 intended to cooperate with a special fitting tool, see FIG. 2.

The conical upper part 17 allows the dental bridge to be arranged on the distance members even when there is no parallelism between two or more distance members.

As mentioned above, the distance screw 7 is provided with a male part having a threaded part 8, and furthermore has an unthreaded middle part 20 whose diameter essentially corresponds to the diameter of the internal thread of the fixture. The upper part of the distance screw, which is accommodated within the conical delimiting surface which is defined by the gold cylinder 4, comprises a lower, wider cylindrical part 21 which adjoins the internal tubular surface of the sleeve-shaped element and which at the top merges, via a downwardly turned annular collar 22, into an upper conical part 23 which is accommodated within and adjoins the inner wall of the gold cylinder and forms a conical extension of the conical part 17 of the sleeve-shaped element. Like the sleeve-shaped element 5, the conical part 23 is provided with an external hexagonal recess 24 for cooperation with a special fitting tool, see FIG. 2.

The upper part of the distance screw is provided with an internal, threaded bore 25 for a gold screw 26 which secures the gold cylinder 4 against the annular collar 16 of the sleeve-shaped element. The annular collar 22 of the distance screw bears against the upper end surface of the sleeve-shaped element and secures the latter to the fixture.

The distance member is designed to cooperate with a special fitting tool consisting of a tightener 27 with a hexagonal recess 28 which cooperates with the hexagon 24 on the upper conical part 23 of the distance screw, and a counterstay 29 which cooperates with the external hexagonal surface 12 of the sleeve-shaped element. The counterstay 29 is tubular in order to permit passage of the tightener 27 through its continuous inner hole 30.

Figure 2:
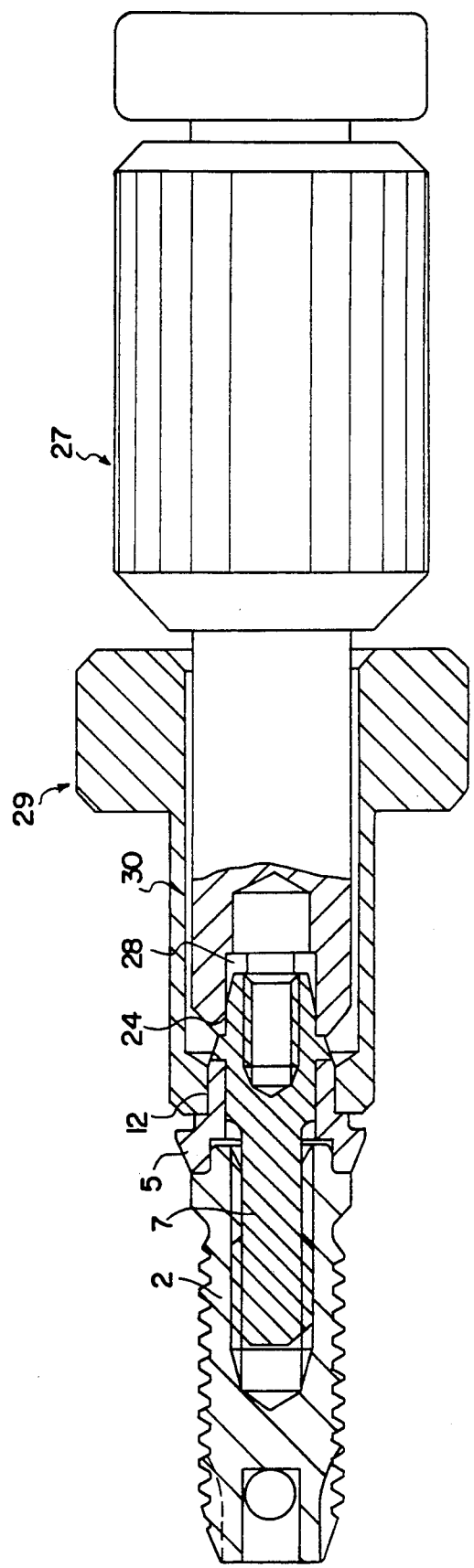
FIG. 2 shows how the distance member cooperates with a fitting tool.

The distance member is arranged on the securing element in the following manner. After an unloaded healing phase of 3-6 months, when the securing element has been able to grow onto the jaw, the fixture is exposed in order to permit fitting of the distance member. The sleeve-shaped element 5 is arranged on the upper part of the fixture in such a way that the base part of the element bears against the annular collar 10 of the fixture. In this position, the base part connects with the hexagonal engagement part 12 of the fixture and cannot be turned around in relation to the fixture. The sleeve-shaped element is locked securely on the fixture with the aid of the distance screw 7 which is screwed down into the bore in the fixture with the aid of the fitting tool, which is shown in FIG. 2, in which respect it is ensured that the tubular counterstay 29 engages against the hexagonal part 12 of the sleeve-shaped element and the tightener 27 is passed through the counterstay and engages in the hexagonal part 24 of the distance screw. Upon fitting of the distance member, torques of similar magnitude but counter-directed are applied to the two parts of the fitting tool, in which respect the fixture is unloaded during the actual fitting.

By means of having a good fit between a) the counterstay 29 and the hexagonal upper part of the sleeve-shaped element, b) the upper hexagonal part 24 of the distance screw and the tightener 27, and c) the distance screw and the sleeve-shaped element, at the same time as having a suitable play between the tightener 27 and the continuous hole 30 in the counterstay, a securing function is obtained, on the one hand, between the sleeve-shaped element and the distance screw and, on the other hand, between the tightener and the counterstay of the fitting tool.

Figure 3C:
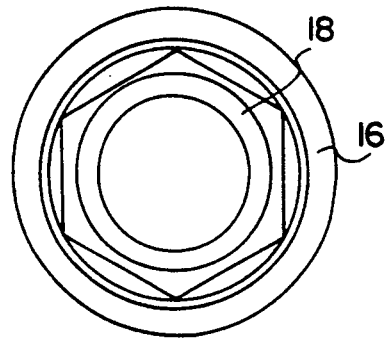
FIG. 3 shows the distance element separately.
Figure 3A:
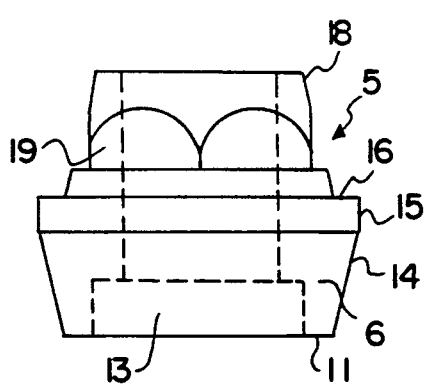
Figure 3B:
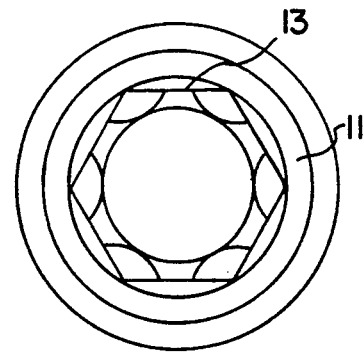

FIG. 3 shows the sleeve-shaped distance element separately, from the side (FIG. 3a), from below (FIG. 3b) and from above (FIG. 3c).

Figure 4:
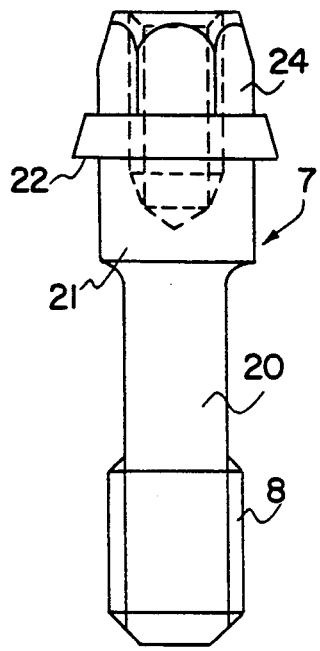
FIG. 4 shows the distance screw separately.

FIG. 4 shows the distance screw separately in a side view.

The invention is not limited to the embodiment which has now been described, but can instead be varied within the scope of the subsequent patent claims In particular, the height of the sleeve-shaped element can be varied by offering the cylindrical part 15 in different lengths.

I claim:

1. A two-part distance member for a tooth implant including a fixture having a lower end anchored in the jaw and an upper portion, said distance member comprising:

a sleeve-shaped element which has a lower portion connectable to the upper portion of the fixture and an upper portion having an end surface; and a distance screw provided with a) an externally threaded forward part for engaging into a threaded bore of the fixture;

a proximal portion having a bore therein for receiving means for securing a prosthesis construction onto the distance member; and an outwardly projecting collar provided intermediate said forward part and proximal portion, said collar having a lower end surface adapted to rest onto the end surface of the upper portion of said sleeve-shaped element to secure said sleeve-shaped element on the fixture upon screwing of said threaded forward part of said distance screw into said bore of the fixture; and wherein the upper portion of said sleeve-shaped element includes a first conical outer surface and said proximal portion of said distance screw includes a second conical outer surface forming an extension of said first conical outer surface of said sleeve-shaped element such that said distance member is adapted to be accommodated into a conical upwardly converging delimiting surface.

2. A two-part distance member according to claim 1 wherein said delimiting surface is defined by a conical gold cap adapted to be embedded in a prosthesis construction.

3. A two-part distance member according to claim 1, wherein said sleeve-shaped element and said distance screw each comprises an external engagement part for a fitting tool.

4. A two-part distance member according to claim 1, wherein said first conical outer surface of the upper portion of said sleeve-shaped element is provided with a hexagonal engagement part for a tubular counterstay of a fitting tool and said second conical outer surface of the proximal portion of said distance screw also includes an external hexagonal engagement part for a tightener of a fitting tool, which tightener is designed to be introduced through a continuous channel in the counterstay.

5. A two-part distance member according to claim 1, wherein said lower portion on the sleeve-shaped element is a conical, downwardly narrowing base part adapted for bearing against a shoulder part formed on the upper portion of the fixture, and wherein said sleeve-shaped element further includes a short cylindrical intermediate part which merges, via an annular collar, into a conical upper portion.

6. A two-part distance member according to claim 5, wherein the conical base part of the sleeve-shaped element has an internal hexagonal engagement part which is adapted to cooperate with a corresponding hexagonal portion of the upper portion of the fixture.

7. A two-part distance member according to claim 1, wherein an annular collar of the sleeve-shaped element forms a bearing surface for a base portion of a conical gold cap embedded in the prosthesis construction.

* * * * *